(12) United States Patent
Augustine

(10) Patent No.: US 11,271,281 B2
(45) Date of Patent: *Mar. 8, 2022

(54) SURGICAL SPONGES WITH FLEXIBLE RFID TAGS

(71) Applicant: Augustine Biomedical and Design, LLC, Eden Prairie, MN (US)

(72) Inventor: Scott D. Augustine, Deephaven, MN (US)

(73) Assignee: Augustine Biomedical and Design, LLC, Eden Prairie, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 16/853,112

(22) Filed: Apr. 20, 2020

(65) Prior Publication Data

US 2020/0321684 A1 Oct. 8, 2020

Related U.S. Application Data

(63) Continuation of application No. 16/561,005, filed on Sep. 4, 2019, now Pat. No. 10,637,125, which is a (Continued)

(51) Int. Cl.
*H01Q 1/22* (2006.01)
*A61F 13/36* (2006.01)
(Continued)

(52) U.S. Cl.
CPC .......... *H01Q 1/2225* (2013.01); *A61F 13/36* (2013.01); *A61F 13/44* (2013.01); *G06K 19/025* (2013.01);
(Continued)

(58) Field of Classification Search
CPC ............... G06Q 10/0875; G06K 19/08; G06K 19/07722; G06K 19/025; G06K 19/07758;
(Continued)

(56) References Cited

U.S. PATENT DOCUMENTS 5,045,080 A * 9/1991 Dyer ........................ A61L 15/18
604/362
5,650,596 A 7/1997 Morris et al.
(Continued)

FOREIGN PATENT DOCUMENTS

WO 2006086603 A2 8/2006

*Primary Examiner* — Thien T Mai
(74) *Attorney, Agent, or Firm* — Fredrikson & Byron, P.A.

(57) ABSTRACT

A surgical sponge is provided, having a radiofrequency (RF) tag positioned interior thereto. The RF tag has a base layer with at least one tab projecting from an outer perimeter of thereof. The RF tag has a first protective layer with at least one tab projecting from the outer perimeter of the RF tag and generally aligned with the at least one tab of the base layer and an RF identifier laminated between the base layer and the first protective layer. The RF identifier has an antenna, and an electrically responsive member. The antenna can be a metal foil loop antenna etched on to the base layer. The RF identifier can include additional metal foil provided on the base layer when the metal foil loop antenna is etched on to the base layer, the additional metal foil configured to enhance x-ray opacity of the sponge.

23 Claims, 8 Drawing Sheets

Related U.S. Application Data continuation of application No. 15/695,575, filed on Sep. 5, 2017, now Pat. No. 10,461,397.

(51) Int. Cl.
    *G06K 19/02*     (2006.01)
    *H01Q 7/00*     (2006.01)
    *H01Q 1/40*     (2006.01)
    *G06K 19/077*     (2006.01)
    *A61F 13/44*     (2006.01)

(52) U.S. Cl.
    CPC . *G06K 19/07722* (2013.01); *G06K 19/07758* (2013.01); *H01Q 1/40* (2013.01); *H01Q 7/00* (2013.01)

(58) Field of Classification Search
    CPC ...... A61B 50/37; A61B 90/98; H01Q 1/2225; H01Q 7/00; H01Q 1/40; H01Q 1/38; H01Q 1/22; A61F 13/44; A61F 13/36; A61F 2002/3067; A61F 7/08; A61F 2002/30604
    See application file for complete search history.

(56) References Cited

U.S. PATENT DOCUMENTS

| | | | |
|---|---|---|---|
| 5,859,587 A | 1/1999 | Alicot et al. | |
| 5,914,862 A | 6/1999 | Ferguson et al. | |
| 5,923,001 A | 7/1999 | Morris et al. | |
| 6,026,818 A | 2/2000 | Blair et al. | |
| 6,496,112 B1 | 12/2002 | Vega | |
| 6,998,541 B2 | 2/2006 | Morris et al. | |
| 8,105,296 B2 | 1/2012 | Morris et al. | |
| 8,181,860 B2 | 5/2012 | Fleck et al. | |
| 8,256,674 B2 | 9/2012 | Fleck et al. | |
| 8,279,068 B2 | 10/2012 | Morris et al. | |
| 8,479,989 B2 | 7/2013 | Fleck et al. | |
| 8,576,076 B2 | 11/2013 | Morris et al. | |
| 8,985,446 B2 | 3/2015 | Fleck et al. | |
| 9,289,943 B2 | 3/2016 | Halberthal et al. | |
| 9,414,973 B2 | 8/2016 | Fleck et al. | |
| 9,530,036 B2 | 12/2016 | Fleck et al. | |
| 2003/0066537 A1* | 4/2003 | Fabian | G01V 15/00 128/899 |
| 2004/0129279 A1 | 7/2004 | Fabian et al. | |
| 2005/0049564 A1 | 3/2005 | Fabian | |
| 2006/0065739 A1 | 3/2006 | Falls, Jr. et al. | |
| 2006/0241396 A1* | 10/2006 | Fabian | A61B 5/06 600/424 |
| 2008/0018432 A1* | 1/2008 | Volpi | G01S 13/825 340/10.3 |
| 2008/0024278 A1 | 1/2008 | Volpi et al. | |
| 2008/0069736 A1* | 3/2008 | Mingerink | B65D 75/52 422/400 |
| 2008/0106419 A1 | 5/2008 | Sakama et al. | |
| 2009/0096629 A1 | 4/2009 | Sprowl et al. | |
| 2011/0002107 A1 | 1/2011 | Tanaka et al. | |
| 2011/0090050 A1* | 4/2011 | MacFarland | G08B 5/40 340/8.1 |
| 2011/0174877 A1 | 7/2011 | Fleck et al. | |
| 2013/0001305 A1 | 1/2013 | Fleck et al. | |
| 2015/0216610 A1* | 8/2015 | Augustine | G06Q 10/0875 235/385 |
| 2016/0004952 A1* | 1/2016 | Mei | G06K 19/07762 235/488 |
| 2016/0171262 A1 | 6/2016 | Fleck et al. | |

\* cited by examiner

SURGICAL SPONGES WITH FLEXIBLE RFID TAGS

PRIORITY CLAIM

This application is a continuation of U.S. patent application Ser. No. 16/561,005, filed Sep. 4, 2019, entitled "Surgical Sponges with Flexible RFID Tags," which is a continuation of U.S. patent application Ser. No. 15/695,575, filed Sep. 5, 2017, entitled "Surgical Sponges with Flexible RFID Tags," the entire contents of which are incorporated herein by reference in their entirety.

BACKGROUND

Surgical sponges are commonly used during surgical procedures to absorb body fluids, mostly blood, of the patient both inside the incision and around the site of surgery. Sponges of this nature are usually made of an open ended absorbent fabric such as woven cotton. When used, surgical sponges become saturated with blood, alter in size and shape and therefore become hard to distinguish from body tissue and each other. For this reason, surgical sponges can be hard to identify and account for both during and after a surgical procedure. Surgical sponges can be inadvertently left inside the patient at the end of surgery. This problem can become magnified in larger surgical procedures where there are a large number of sponges used.

Surgical items may have to be counted before and after surgical procedure. Surgical sponges can be a difficult item to account for before, during and especially after a surgical procedure. Typically medical personnel count these items by hand, based on human visual detection in the body and visual detection and counting to differentiate one sponge from another and account for the sponges when outside the body. If a sponge count taken during or after a procedure does not match the sponge count taken before the procedure, an x-ray can be taken of the surgical site to detect whether or not the missing sponge is still in the patient.

Thus, this method is prone to human error and is therefore unreliable and inefficient. The large amount of time involved in differentiating the sponges from one another and accounting for them leads to large costs. Additionally, the unreliable nature of the method can lead to miscounted sponges resulting in surgical sponges being inadvertently retained inside the patient. Such issues may adversely affect not only the health of the patient, but may also prove costly to the hospital and insurance companies involved.

SUMMARY

In some embodiments of the present disclosure, substantially flat antennae are used to allow lamination between two or more layers of polymeric film. The substantially flat antennae may be loop-shaped or any other suitable shape. These antennae may be made from an etched metal foil applied to a base film layer of stretch-resistant polymeric film. RFID tags of this construction are commonly referred to as "inlay tags." Alternately, in some embodiments the antennae may be made of multiple loops of wire.

In some embodiments, an electrically responsive member is electrically connected to the antenna. An electrically responsive member may include an integrated circuit (IC) chip, a capacitor, a resistor, other electrical components or combinations of these components which are electrically connected to the antenna creating an identifier. If the identifier includes an IC chip, it may be called a Radio Frequency Identification (RFID) identifier. If the identifier includes a capacitor with or without a resistor, it may be called a Radio Frequency (RF) or Low Frequency identifier.

In some embodiments, a planar and/or flexible identifier can be laminated between two or more layers of polymeric film creating a flat, flexible tag. The planar and/or flexible tag may also be mechanically durable, waterproof and able to withstand sterilization.

In some embodiments, the inlay identifier includes a base layer of stretch-resistant polymeric film that reduces the chances of fracturing of metal foil antennae traces during stretching and bending. In some embodiments, a single protective layer of polymeric film may be laminated to the base layer to cover and protect the exposed inlay identifier.

In some embodiments the inlay identifier or wire loop identifier may be laminated between two or more protective film layers. The protective film layers may be made of flexible polymeric film that may be relatively resistant to tearing.

White sponge material that has absorbed blood may turn red and may resemble tissue. Accordingly, in some embodiments, the protective layer of polymeric film may be colored. In some such embodiments, the color may other than a clear color to make the protective layer more visible to the surgeon. Bright colors that contrast blood and tissue may be used in some advantageous aspects of the present disclosure. In some embodiments, materials or colors that "fluoresce" in natural light may be used. In some embodiments, materials or colors that "fluoresce" when illuminated by UV light or colored lights may be included in the protective film layers or coated on to the film. In some embodiments, reflective materials may be included in or on the protective film layer.

In some embodiments, the one or more protective film layers maybe made of a substantially hydrophobic polymeric material to reduce the chances of blood from coating the film. Alternately, a hydrophobic material may be coated on to the protective layers.

In some embodiments, the base film layer with its attached antenna and electrically responsive member bonded to one or more protective film layers may be called an RFID tag or RF tag. The outline shape of the tag may generally follow the shape and size of the sponge. Alternately, outline shape of the tag may be slightly larger than the general outline of the identifier within the tag. The antenna of the identifier may be circular, oval, square, rectangular, elongate rectangular or even complex shapes such as a clover-shape. Therefore the tags can be any corresponding shape as well. The size and shape of the antenna can determine the limits of the size of the tags.

In some embodiments, when the antenna is circular, square or rectangular, there is a space within the inner perimeter of the antenna that is void of metal foil traces. In some embodiments, the base film layer and the one or more protective film layers within the area defined by the inner perimeter of the antenna trace may be removed, creating a hole through the central area of the tag. This hole may increase the flexibility and the overall stretch-ability and the ability to deform like gauze fabric so that the tag feels like it is the sponge rather than being a sheet of plastic interposed between the layers of the gauze sponge.

In some embodiments, some of the material of the base and protective film layers may be left extending outward from the outer perimeter of the tag. The material may be in the shape of one or more tabs extending radially outward.

In some embodiments, some of the material of the base and protective film layers may be left within the perimeter of the hole in the tag. The material may be in the shape of one or more tabs extending radially inward from the inner perimeter of the hole on the tag.

In some embodiments, the tabs extending inward into the hole or outward from the outer perimeter of the tag are used for anchoring the tag to the sponge without damaging the fragile antenna.

In some embodiments, the tag can be attached to the sponge by sewing through both the sponge material and the base and protective film layers of the tag. Sewing through the one or more tabs can reduce the chance of cutting a foil trace of the antenna or a wire of the antenna with the sewing needle.

In some embodiments, the one or more tabs become a safe area for heat bonding the tag to the sponge. Heat bonding may be accomplished by applying a hot object to one or more layers of the sponge fabric while pushing them firmly down onto the one or more layers of protective film layer. The heated object warms and partially melts the polymeric film embedding the fibers of the sponge into the melted film.

In some embodiments, the tabs that allow heat bonding or sewing without damaging the metal foil or conductive ink antenna traces can be used. Such tabs may permit an automated manufacturing process to be used in making the surgical sponges. This disclosure provides a method of making surgical sponges with an attached, flexible RFID or RF inlay tag. The attachment location between the sponge and the tag may be at the one or more tabs. Because the tabs are geographically separated from the electrically functional parts of the identifier, less precision is sufficient when applying pressure and heat or piercing with sewing needles to avoid damaging the identifier. In some embodiments this automated manufacturing process may be used to manufacture surgical sponges with markers made of one or more layers of plastic film but not including RFID or RF identifiers.

In some embodiments, the metal foil inlay identifier or the metal wire of a loop antenna creates a densely radio-opaque area easily visualized by x-ray. In some embodiments, excess metal foil may be left on the base film layer during the etching process, substantially increasing the x-ray opacity of the metal foil at no extra cost.

In some embodiments, enhanced surgical sponge visualization and/or enhanced x-ray opacity may be desirable without RFID. Inexpensive and easily identifiable markers may be made similarly to the RFID tags previously discussed in this disclosure except that the inlay identifier is omitted. The markers may be made of one or more layers of colored polymeric film with or without a metal foil layer for x-ray opacity. The marker may then be attached by heat bonding, sewing or adhesives between the layers of the surgical sponge as previously described. The marker may be any size or shape In some embodiments, the sponges are spread out so that their antennae may overlap or crossover but do not stack. Spreading the sponges out also decreases the chances of packaging the wrong number of sponges in the pack at the factory or miscounting during surgery. If each location on the card is occupied by a single sponge, the correct number can be identified with a cursory visual inspection by either a human or a machine.

In some embodiments, the sponge dispensing card may include a pressure sensitive adhesive area designed to anchor the card to the surgical instrument table. This allows for easier dispensing of the sponges from the card.

In addition, certain aspects of the present disclosure include the following numbered embodiments:

1. A surgical sponge with radio-frequency identification (RFID) counting and detection comprising:
    a surgical sponge;
    a flexible RFID identifier that includes an antenna and an electrically responsive member which are laminated between a base film layer and a first protective film layer creating a flexible RFID tag;
    the base film layer is made of a flexible stretch-resistant polymeric film;
    the first protective film layer is made of a flexible tear-resistant polymeric film; wherein, the flexible RFID tag is secured between the layers of the sponge material.
2. The surgical sponge of embodiment 1, wherein the antenna is an etched metal foil loop antenna.
3. The surgical sponge of embodiment 1 or 2, wherein the antenna is a wound wire loop antenna.
4. The surgical sponge of embodiment 1 or any previous embodiment, wherein the antenna is a loop antenna that is substantially square configuration in order to maximize the antenna size relative to the substantially square surgical sponges.
5. The surgical sponge of embodiment 1 or any previous embodiment, wherein the electrically responsive member includes a programmable integrated circuit (IC) chip.
6. The surgical sponge of embodiment 1 or any previous embodiment, wherein the electrically responsive member includes a capacitor.
7. The surgical sponge of embodiment 1 or any previous embodiment, wherein the electrically responsive member includes a capacitor and resistor.
8. The surgical sponge of embodiment 1 or any previous embodiment, wherein the base film layer of stretch-resistant polymeric film is attached to the loop antenna for protecting a foil antenna from tearing and an IC chip from dismounting.
9. The surgical sponge of embodiment 1 or any previous embodiment, wherein the stretch-resistant polymeric films that may be suitable for the first material layer include but are not limited to PET, PP, polyester and nylon.
10. The surgical sponge of embodiment 1 or any previous embodiment, wherein the first protective film layer comprises a tear-resistant polymeric film to prevent tearing of the laminated material layers forming the tag, especially along the series of holes created by sewing or areas of material weaknesses created by heat bonding.
11. The surgical sponge of embodiment 1 or any previous embodiment, wherein the tear-resistant polymeric films that may be suitable for the second material layer include but are not limited to urethane, nylon, PVC.
12. The surgical sponge of embodiment 1 or any previous embodiment, wherein the laminated RFID tag may include one or more additional flexible protective film layers.
13. The surgical sponge of embodiment 1 or any previous embodiment, wherein the flexible film layers are bonded together with an adhesive capable of withstanding temperatures in excess of 250° F. for steam autoclave durability.
14. The surgical sponge of embodiment 1 or any previous embodiment, wherein the thickness of the first protective film layer forces the laminate to bend in a radius rather than a kink, protecting the foil antenna from breaking during bending.
15. A surgical sponge with radio-frequency identification (RFID) counting and detection comprising:
    a surgical sponge;
    a flexible inlay RFID identifier that includes a loop antenna and an electrically responsive member which are laminated between a base layer and a first polymeric protective film layer creating an RFID tag;

the flexible RFID tag is positioned between the base layer and a first polymeric protective film layer of the sponge and is attached to the surgical sponge; wherein
the base layer and first protective layers are removed from a portion of the area of the tag defined by the inner perimeter of the loop antenna, creating a hole through the flexible RFID tag for improved flexibility.

16. The surgical sponge of embodiment 15 or any previous embodiment, wherein the antenna is at least one of: an etched metal foil loop antenna or a wound wire loop antenna.

17. The surgical sponge of embodiment 16 or any previous embodiment, wherein the loop antenna is a substantially square configuration in order to maximize the antenna size relative to the substantially square surgical sponges 18. The surgical sponge of embodiment 15 or any previous embodiment, wherein the electrically responsive member includes at least one of: a programmable integrated circuit (IC) chip or capacitor or capacitor and resistor.

19. The surgical sponge of embodiment 15 or any previous embodiment, wherein the tag includes two or more polymeric protective film layers.

20. The surgical sponge of embodiment 15 or any previous embodiment, wherein at least one of the polymeric protective film layers is made of a flexible tear-resistant film for enhanced durability when sewn.

21. The surgical sponge of embodiment 15 or any previous embodiment, wherein the tag is attached to the sponge by sewing through the tag and sponge material layers.

22. The surgical sponge of embodiment 15 or any previous embodiment, wherein the tag is attached to the sponge by heat bonding the fibers of the sponge to one or more of the polymeric material layers of the tag.

23. The surgical sponge of embodiment 15 or any previous embodiment, wherein one or more tabs of the laminated polymeric material layers project inward from the inner perimeter of the hole, into the hole area of the tag enabling easier sewing or heat bonding of the tag to the sponge.

24. A surgical sponge with radio-frequency identification (RFID) counting and detection comprising:
a surgical sponge;
a flexible RFID identifier that includes an antenna and an electrically responsive member which are laminated between a base layer and a first polymeric protective film layer creating an RFID tag;
the flexible RFID tag is positioned between the layers of the sponge material and is attached to the surgical sponge;
wherein one or more tabs of the laminated polymeric base and protective film layers project outward from the outer perimeter of the tag.

25. The surgical sponge of embodiment 24 or any previous embodiment, wherein the antenna is at least one of: an etched metal foil loop antenna or a wound wire loop antenna.

26. The surgical sponge of embodiment 25 or any previous embodiment, wherein the antenna is a loop antenna that is substantially square configuration in order to maximize the antenna size relative to the substantially square surgical sponges.

27. The surgical sponge of embodiment 24 or any previous embodiment, wherein the electrically responsive member includes at least one of: programmable integrated circuit (IC) chip or a capacitor or capacitor and resistor.

28. The surgical sponge of embodiment 24 or any previous embodiment, wherein the tag includes two or more polymeric protective film layers.

29. The surgical sponge of embodiment 24 or any previous embodiment, wherein the at least one of the polymeric material layers is made of a flexible tear-resistant film for enhanced durability when sewn.

30. The surgical sponge of embodiment 24 or any previous embodiment, wherein the tag is attached to the sponge by sewing through the tag and sponge material layers.

31. The surgical sponge of embodiment 24 or any previous embodiment, wherein the tag is attached to the sponge by heat bonding the fibers of the sponge to one or more of the polymeric material layers of the tag.

32. The surgical sponge of embodiment 24 or any previous embodiment, wherein the one or more tabs projecting outward from the outer perimeter of the tag, enabling easier sewing or heat bonding of the tag to the sponge.

33. The surgical sponge of embodiment 24 or any previous embodiment, wherein the one or more tabs projecting outward from the outer perimeter of the tag project beyond an edge of the sponge when the tag is attached to the sponge.

34. A surgical sponge with radio-frequency identification (RFID) counting and detection comprising:
a surgical sponge;
a flexible inlay RFID identifier that includes an etched metal foil loop antenna and an electrically responsive member which are laminated between a polymeric base film layer and a first protective film material layer creating an RFID tag;
the flexible RFID tag is positioned between the layers of the sponge material and is attached to the surgical sponge; wherein
the etching of the metal foil loop antenna leaves excess metal foil still attached to the polymeric base film layer to enhance x-ray opacity of the sponge.

35. The surgical sponge of embodiment 34 or any previous embodiment, wherein the loop antenna is a substantially square configuration in order to maximize the antenna size relative to the substantially square surgical sponges 36. The surgical sponge of embodiment 34 or any previous embodiment, the electrically responsive member includes at least one of: a programmable integrated circuit (IC) chip, or a capacitor or capacitor and resistor.

37. The surgical sponge of embodiment 34 or any previous embodiment, wherein the tag includes two or more polymeric protective film layers.

38. The surgical sponge of embodiment 34 or any previous embodiment, one or more tabs of the one or more laminated polymeric base and protective film layers project outward from the outer perimeter of the tag, enabling easier attachment of the tag to the sponge.

39. The surgical sponge of embodiment 34 or any previous embodiment, wherein the one or more tabs of the laminated polymeric base and protective film layers projecting outward from the outer perimeter of the tag, also include a layer of metal foil for enhanced x-ray opacity of the sponge.

40. The surgical sponge of embodiment 34 or any previous embodiment, wherein the one or more tabs projecting outward from the outer perimeter of the tag project beyond the edge of the sponge when the tag is attached to the sponge.

41. The surgical sponge of embodiment 34 or any previous embodiment, the polymeric base and protective film layers are removed from a portion of the area of the tag defined by the inner perimeter of the loop antenna, creating a hole through the flexible RFID tag for improved flexibility.

42. The surgical sponge of embodiment 34 or any previous embodiment, one or more attachment tabs of the laminated polymeric base and protective film layers project inward from the inner perimeter of the hole, into the hole area of the tag and also include a layer of metal foil for enhanced x-ray opacity of the sponge.

43. A surgical sponge with radio-frequency identification (RFID) counting and detection comprising:
a surgical sponge;
a flexible RFID identifier that includes an antenna and an electrically responsive member which are laminated between a base film layer and a first protective layer creating a flexible RFID tag;
the flexible RFID tag is positioned between the layers of the sponge material;
wherein one or more of the base film layer and the first protective film layer is made of colored polymeric film for enhanced visibility.

44. The surgical sponge of embodiment 43 or any previous embodiment, wherein the antenna is at least one of: an etched metal foil loop antenna or a wound wire loop antenna.

45. The surgical sponge of embodiment 44 or any previous embodiment, wherein the antenna is a loop antenna that is substantially square configuration in order to maximize the antenna size relative to the substantially square surgical sponges.

46. The surgical sponge of embodiment 43 or any previous embodiment, wherein the electrically responsive member includes at least one of: programmable integrated circuit (IC) chip, or a capacitor, or a capacitor and resistor.

47. The surgical sponge of embodiment 43 or any previous embodiment, wherein the tag includes two or more polymeric protective film layers.

48. The surgical sponge of embodiment 43 or any previous embodiment, wherein the polymeric protective film layer is colored white.

49. The surgical sponge of embodiment 43 or any previous embodiment, wherein the polymeric protective film layer is colored a bright color that contrasts with blood and tissue.

50. The surgical sponge of embodiment 43 or any previous embodiment, wherein the polymeric protective film layer is colored a bright fluorescent colors such as green or yellow.

51. The surgical sponge of embodiment 43 or any previous embodiment, wherein the polymeric protective film layer is colored such that it fluoresces when illuminated by an ultraviolet or other specifically selected light source.

52. The surgical sponge of embodiment 43 or any previous embodiment, the polymeric base and protective film layers are removed from a portion of the central area creating a hole through the polymeric film for improved flexibility.

53. The surgical sponge of embodiment 43 or any previous embodiment, the polymeric protective film layer is hydrophobic repelling blood from coating and obscuring the film.

54. The surgical sponge of embodiment 43 or any previous embodiment, wherein the polymeric protective film layer is hydrophobic relative to the absorbent sponge material repelling blood from coating and obscuring the film.

55. A surgical sponge with a visual identifier comprising:
a surgical sponge;
one or more layers of flexible, nonabsorbent polymeric film is interposed between the fabric layers of the sponge and is attached to the sponge; and
includes one or more tabs of the polymeric film that project beyond the outer edge of the sponge; wherein the layer of polymeric film is colored for enhanced visibility.

56. The surgical sponge of embodiment 55 or any previous embodiment, wherein the polymeric film is colored white.

57. The surgical sponge of embodiment 55 or any previous embodiment, wherein the polymeric film is colored a bright color that contrasts with blood and tissue.

58. The surgical sponge of embodiment 55 or any previous embodiment, wherein the polymeric film is colored a bright fluorescent colors such as green or yellow.

59. The surgical sponge of embodiment 55 or any previous embodiment, wherein the polymeric film is colored such that it fluoresces when illuminated by an ultraviolet or other specifically selected light source.

60. The surgical sponge of embodiment 55 or any previous embodiment, wherein the polymeric film is removed from a portion of the central area creating a hole through the polymeric film for improved flexibility.

61. The surgical sponge of embodiment 55 or any previous embodiment, wherein the polymeric film includes a laminated layer of radio-opaque metal foil across some or all of its surface.

62. The surgical sponge of embodiment 55 or any previous embodiment, wherein the polymeric film is hydrophobic repelling blood from coating and obscuring the film.

63. The surgical sponge of embodiment 55 or any previous embodiment, wherein the polymeric film is hydrophobic relative to the absorbent sponge material repelling blood from coating and obscuring the film.

64. Surgical sponges with radio-frequency identification (RFID) counting and detection comprising:
a plurality of surgical sponges;
a plurality of flexible inlay RFID tags that include a loop antenna and a programmable integrated circuit (IC) chip which are laminated between a base film layer and a first protective film layer;
the flexible inlay RFID tags are attached to the surgical sponges;
wherein the sponges with attached RFID tags are loosely attached to a dispensing card that arranges the sponges in a partially overlapping condition so that the loop antennae cross each other but do not closely stack on each other.

65. The surgical sponges of embodiment 64 or any previous embodiment, wherein loop antennae are substantially square and are oriented on the substantially square surgical sponges with the straight portions of the loop antennae substantially parallel to the straight edges of the sponges.

66. The surgical sponges of embodiment 65 or any previous embodiment, wherein the loop antennae are substantially circular and are sized to fit within the substantially square surgical sponges.

67. The surgical sponges of embodiment 64 or any previous embodiment, wherein the sponges are oriented diagonally on the card so that the most overlapping point is a corner.

68. The surgical sponges of embodiment 64 or any previous embodiment, wherein the card includes adhesive for securing the sponges.

69. The surgical sponges of embodiment 64 or any previous embodiment, wherein he card includes slits for securing the sponges.

70. The surgical sponges of embodiment 64 or any previous embodiment, wherein he slits are horizontal or semicircular and are sized to allow ⅓ to ⅔ of the area of the sponge to fit through the slit and thus be positioned on the opposite side of the card.

71. The surgical sponges of embodiment 64 or any previous embodiment, wherein the card include an area of adhesive on its back side for removably attaching the dispensing card to the surgical instrument table.

DETAILED DESCRIPTION

Some embodiments of this disclosure provide a surgical sponge having an absorbent body and one or more identifiers attached to or embedded within the sponge. Certain embodiments of this disclosure also provide a surgical sponge counting and detection system for counting surgical sponges, and a method for counting and detection of surgical sponges. The present disclosure may reduce the likelihood that a sponge will remain in a patient after surgery and may reduce the time involved in accounting for sponges during surgery.

Figure 1:
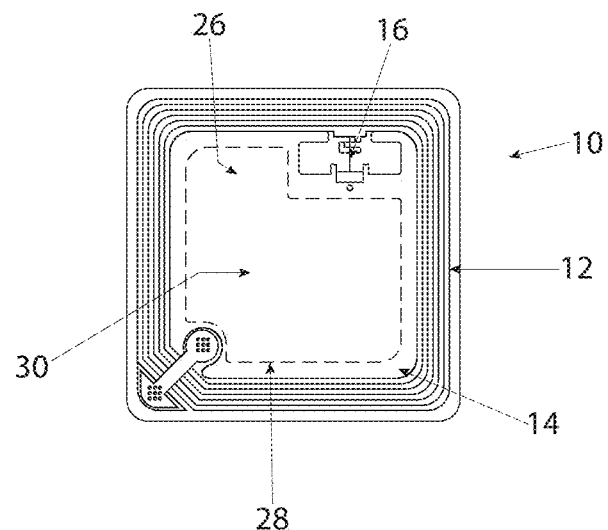
FIG. 1 is a top view of an identifier according to a non-limiting illustrative embodiment.
Figure 2:
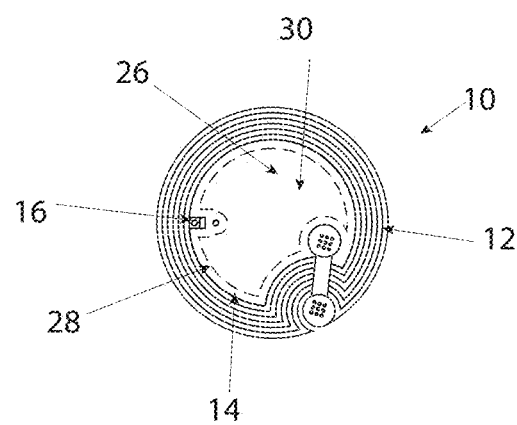
FIG. 2 is a top view of an identifier according to another non-limiting illustrative embodiment.
Figure 3:
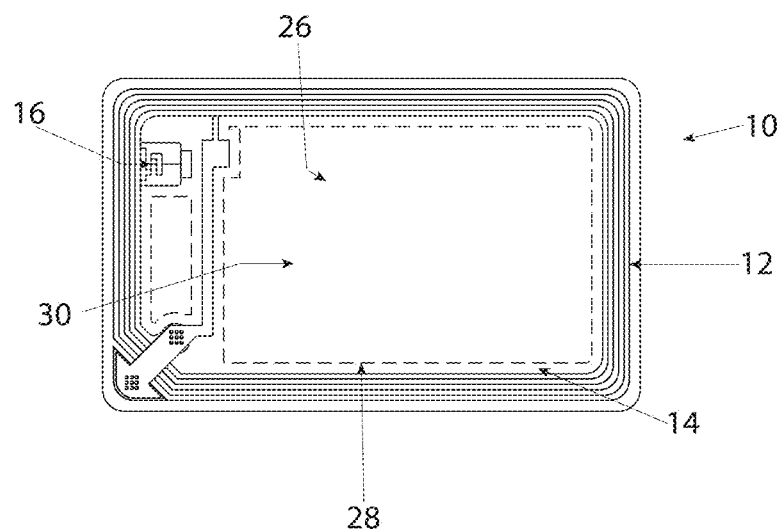
FIG. 3 is a top view of an identifier according to another non-limiting illustrative embodiment.

FIGS. 1, 2 and 3 illustrate identifiers for surgical sponges according to an embodiment of the present disclosure. In the illustrated embodiments, the identifiers may be Radio Frequency (RF) or Radio Frequency Identification (RFID) identifiers may be made in a relatively flat configuration. While FIG. 1 illustrates the identifier in a generally square shape, FIG. 2 illustrates the identifier in a generally circular shape, and FIG. 3 illustrates the identifiers to be of a generally rectangular shape. However, identifiers can be virtually any other shape. In some embodiments, the identifier 10 may consist of an antenna 12 which may be made of etched metal foil traces or printed traces of conductive ink or multiple loops of wire. Other antenna constructions are anticipated.

With reference to FIGS. 1, 2 and 3, in non-limiting illustrative embodiments, the antenna 12 is attached to a base layer 14. In the case of an etched metal foil antenna, the metal foil may be applied to the base layer 14 before the etching process occurs. In the case of a printed conductive ink antenna, the conductive ink may be printed on to the base layer 14. The base layer 14 provides structural strength for the very fragile metal or ink traces, especially preventing stretching that would fracture the traces. In the case of antennae made of multiple loops of wire, the wire loops may be attached to the base layer 14 during or after the winding process.

In some advantageous aspects of the disclosure, the base layer 14 can be made of a relatively stretch-resistant polymeric film, to prevent the identifier 10 from stretching and fracturing the fragile antenna traces 12. Suitable stretch-resistant polymeric films include but are not limited to: polyethylene terephthalate (PET), polypropylene (PP), polyester (PE) and nylon. In some embodiments, paper may be substituted for the stretch-resistant polymeric base film layer 14.

Referring again to the non-limiting illustrative embodiments of FIGS. 1-3, an electrically responsive member 16 is electrically connected to the antenna 12. The electrically responsive member 16 may include an integrated circuit (IC) chip.

In some embodiments, the electrically responsive member 16 may include a capacitor with our without a resistor or other electrical components. In this case, the resulting identifier 10 is a Radio Frequency (RF) or Low Frequency (LF) identifier.

In some embodiments, when the identifier 10 is made with an etched foil antenna or a printed conductive ink antenna 12, the identifier 10 can called an "inlay." In some such embodiments, the identifiers 10 can be made by an economical, fully automated process with excellent quality controls.

Figure 4:
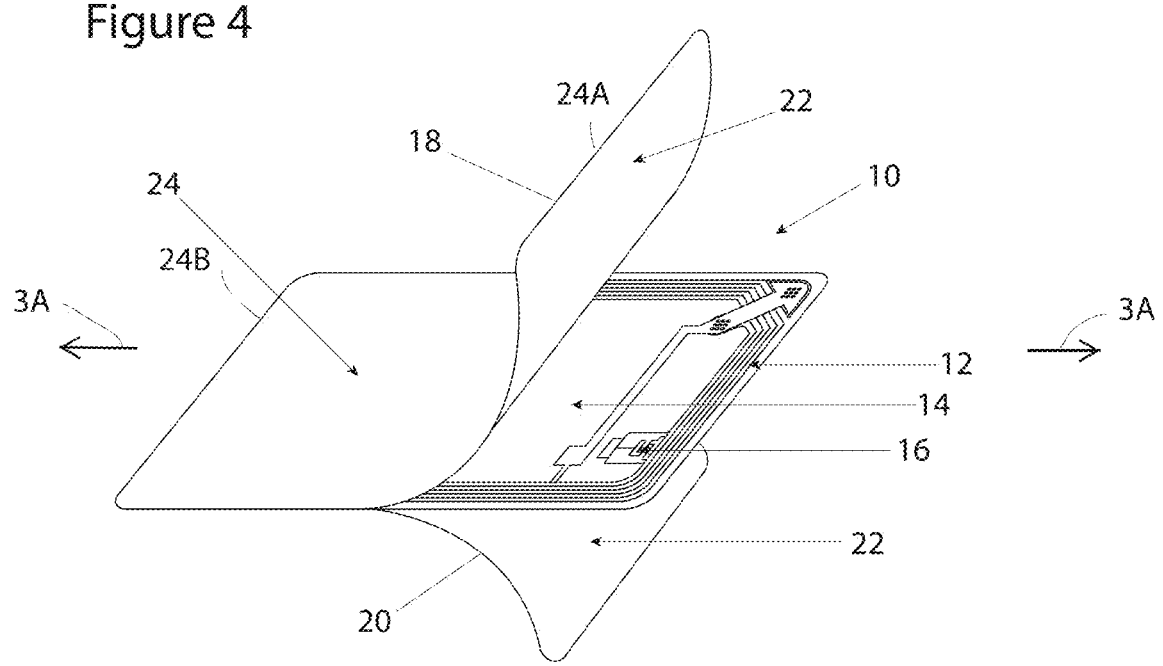
FIG. 4 is a top perspective view of a tag according to a is a non-limiting illustrative embodiment having the identifier of FIG. 3.

As shown in the illustrative embodiment of FIG. 4, inlay identifier 10 may be laminated between one or more protective film layers 18, 20. First protective film layer 18 may be laminated over the exposed etched metal foil or printed conductive ink traces 12 and the electrically responsive member 16. First protective film layer 18 protects certain components of the identifier 10 from mechanical damage as well as damage from liquids such as blood. First protective film layer 18 also reduces the chance of liquids (e.g., blood or medical fluids) from electrically shorting out the RFID or RF circuit. The laminated identifier can also be referred to as a tag 24.

With continued reference to the non-limiting exemplary embodiment of FIG. 4, a second protective film layer 20 may be laminated to the identifier. The second protective film layer 20 can be opposite the first protective film layer 18.

This configuration sandwiches the identifier 10 in between two protective film layers 18, 20, for added security and durability. Further, when laminated on both sides, the identifier 10 can sometimes be referred to as a tag 24.

In certain aspects of the disclosure, the protective film layers 18, 20 may be made of polymeric film that is flexible and may also be relatively resistant to tearing. Suitable tear-resistant polymeric films include but are not limited to: urethane, nylon and polyvinylchloride (PVC).

The thickness of the one or more protective film layers 18, 20 may be greater than 0.003 in. (3 mil.) in some exemplary embodiments. This may reduce kinking of the inlay antenna 12 (and associated fracture) during severe bending because the radius of the bend may be greater than the 0.003 in. thickness of the protective film.

In some embodiments, the base layer 14 is bonded to one or more protective film layers 18, 20. The layers may be bonded together using adhesive 22. Suitable adhesives include but are not limited to: pressure sensitive adhesives (PSA), hot melt adhesives and various liquid applied adhesives that require curing. Curing may include the application of UV light. In the case of other adhesives such as epoxy, curing may include the addition of a catalyst.

While some desirable properties of the adhesive 22 are mentioned above, it may be additionally desirable for the adhesive 22 to be flexible, water resistant, heat tolerant (up to steam autoclave temperatures, 250° F.), relatively fast curing and durable.

In some embodiments, the base layer 14 and/or the one or more protective film layers 18, 20 may be plasma etched prior to the application of adhesive 22 to improve the adherence of the adhesive 22 to the film layers 14, 18, 20. Alternatively, the base layer 14 and/or the one or more protective film layers 18, 20 may be bonded together using heat bonding, ultrasound (US) bonding, radio-frequency (RF) bonding or other bonding methods.

As shown in FIGS. 1-3 and 5 in some embodiments when the antenna 12 is square, circular, or rectangular, a space 26 is present within the inner perimeter of the antenna that is void of metal foil traces.

As shown by the embodiments of FIGS. 1-3,5 and 6, the base layer 14 and the one or more protective film layers 18, 20 within the area 26 defined by the inner perimeter of the antenna trace 28 may be removed, creating a hole 30 through the central area of the tag 24. Removing the layers of film substantially in the middle of the tag 24 may improve the flexibility of the tag. The hole 30 in the tag 24 can allows a stretching or planar deformation of the tag 24 (e.g., along arrows 3A indicated in FIG. 4) that cannot generally occur with complete sheets of polymeric film. In addition, the tag 24 may be flexible, such that edges 24A, 24B may be brought toward each other, permitting the tag 24 to be bent. The hole 30 in the tag 24 allows the tag to feel much like the layers of the fabric sponge that it will be embedded in, rather than feel like a sheet of plastic in the sponge. The flexible and stretchable tag 24 can thus be generally inconspicuous to touch when attached to the surgical sponge.

Referring back to the illustrative embodiments of FIGS. 1-3, the hole 30 in the identifier 10 or tag is substantially square, circular, or rectangular, though other shapes including oval and irregular shapes are contemplated within the scope of the present disclosure. The shape of the hole 30 may match the shape of the tag 10 and may also be square, circular or rectangular. The hole 30 may advantageously include rounded corners to reduce the chances of tearing.

In some embodiments, if the antenna shape is more complex (e.g., a four-leaf clover), there may be cuts made through the base and protective film layers between the antenna traces, without removing film material to create a hole. The cuts, even in the absence of holes, improve the flexibility and stretch-ability of the tag. Alternately, the cuts may be made inward from the outer perimeter of the tag.

In some such embodiments, cuts may be made through the base and protective film layers in any areas of the tag not occupied by either the antenna or electrically responsive member. The cuts improve the flexibility and stretch-ability of the tag, making it feel more like a surgical sponge.

Figure 5:
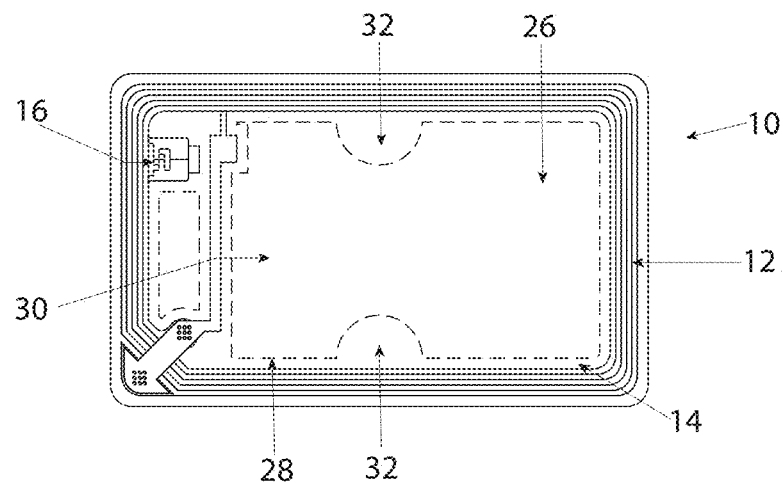
FIG. 5 is a top view of an identifier according to a non-limiting illustrative embodiment.
Figure 6:
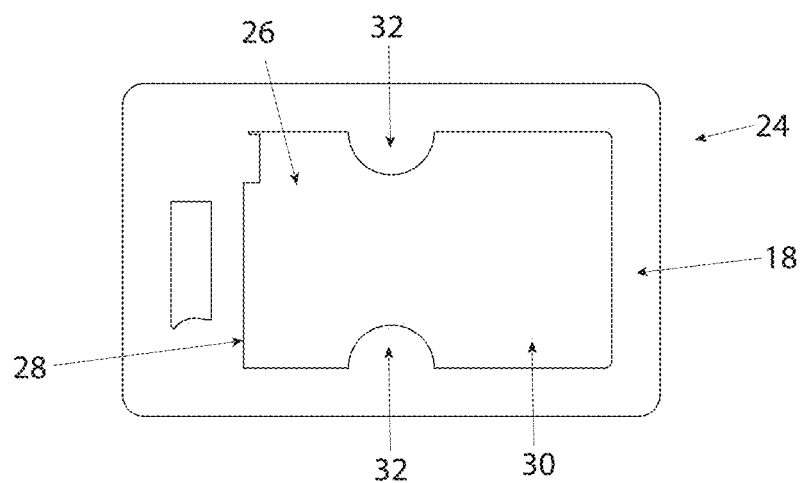
FIG. 6 is a top view of a tag according to a is a non-limiting illustrative embodiment having the identifier of FIG. 5.
Figure 10:
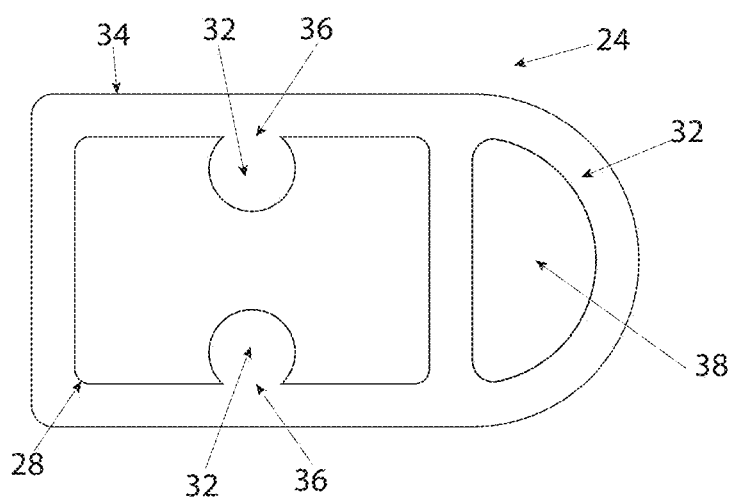
FIG. 10 is a top view of a tag according to a is a non-limiting illustrative embodiment having the identifier of FIG. 8.

As shown by the non-limiting illustrative embodiments of FIGS. 5 and 6, some of the material of the base 14 and protective film layers 18, 20 may be left within the perimeter 28 of the hole 30 in the tag 24. The film layers of material may be in the shape of one or more tabs 32 extending radially inward from the inner perimeter 28 of the hole 30. The tabs 32 can be any shape or size, including less than 0.5 inches square. As shown in FIG. 10, if flexibility is desired, tabs 32 may be attached to the tag 24 by way of a narrowed isthmus 36 of laminated base 14 and protective film layers 18, 20.

Figure 7:
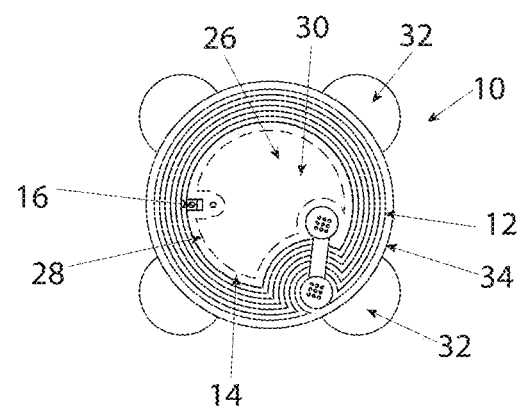
FIG. 7 is a top view of an identifier according to a non-limiting illustrative embodiment.
Figure 8:
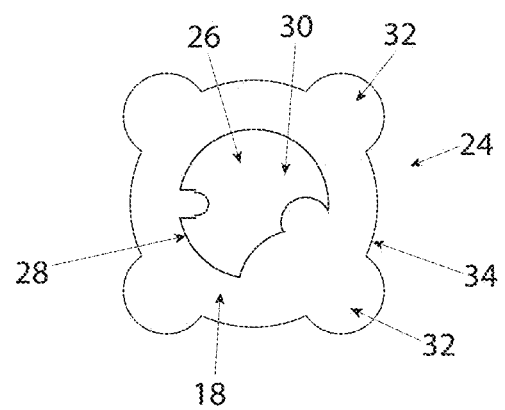
FIG. 8 is a top view of a tag according to a is a non-limiting illustrative embodiment having the identifier of FIG. 7.

As shown by the non-limiting exemplary embodiment of FIGS. 7 and 8, some of the material of the base 14 and protective film layers 18, 20 may be left extending outward from the outer perimeter 34 of the tag 24. The material may be in the shape of one or more tabs 32 extending radially outward. The tabs 32 can be of any shape or size, including less than 0.75 inches square. If flexibility is desired, tabs 32 may be attached to the tag 24 by way of a narrowed isthmus 36 of laminated base 14 and protective film layers 18, 20.

Figure 9:
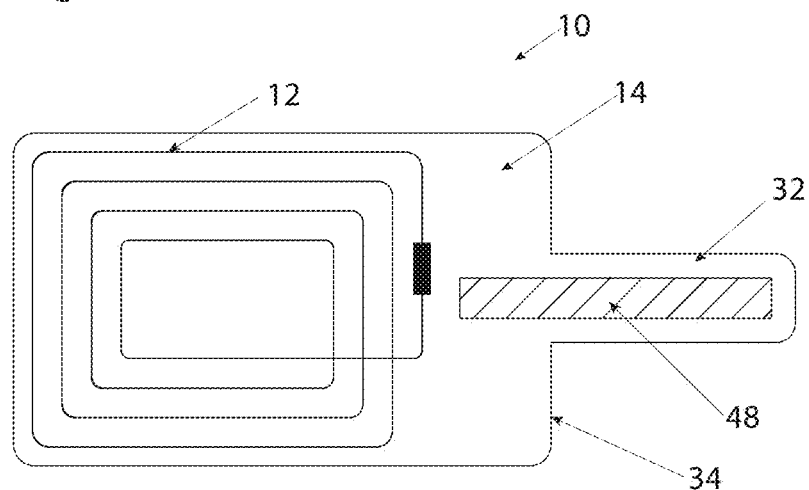
FIG. 9 is a top view of an identifier according to a non-limiting illustrative embodiment.

Referring now to the non-limiting exemplary embodiment of FIG. 9, the tab 32 may be in the form of one or more elongate protrusions from the outer perimeter 34 of the tag 24. In such embodiments, it may be advantageous if the elongate protrusion 32 extends beyond the border of the sponge (not shown) that the tag 24 may be embedded within. In this exposed position, the tab 32 may provide added visibility of a sponge having blood to the surgeon or a handle to grasp by the surgeon or nurse. This may be useful when removing a sponge during laparoscopic surgery. The exposed tab 32 may provide enhanced visibility, differentiation and pattern recognition to the nurse or surgical technician for identifying individual sponges. In this exposed position, the tab 32 may provide an object for accurate indexing during both the placement and securement of the tag to the sponge during an automated manufacturing process and an object for machine vision optical inspections and counting during manufacturing, or other uses.

FIG. 10 illustrates a tag according to another non-limiting exemplary embodiment. As seen in FIG. 10, the tab 32 may be a substantially semicircular or "D" shaped protrusion from the outer perimeter 34 of the tag 24. An optional hole 38 may be provided in the central portion of the tab 32. Tab 32 can protrude from the outer perimeter 34 of the tag 24. The tab 32 can be of any shape. In some embodiments, it may be advantageous if the tab 32 extends beyond the border of the sponge (not shown) that the tag 24 may be embedded within. In this exposed position, the tab 32 may provide added visibility of a sponge having blood to the surgeon or a handle to grasp by the surgeon or nurse. This may be useful when removing a sponge during laparoscopic surgery. The exposed tab 32 may provide enhanced visibility, differentiation and pattern recognition to the nurse or surgical technician for identifying individual sponges. In this exposed position, the tab 32 may provide an object for accurate indexing during both the placement and securement of the tag to the sponge during the manufacturing process and an object for machine vision optical inspections and counting during manufacturing, or other uses.

Referring back to FIGS. 6 and 8, the tabs 32 may, optionally, extend inward into the hole 30 or outward from the outer perimeter 34 of the tag 24 are used for anchoring the tag 24 to the sponge (not shown) without damaging the fragile antenna. As shown in FIGS. 5 and 7, the tabs 32 can be spatially separated from the antenna trace 12 and electrically responsive member 16 of the inlay identifier 10. Therefore, the attachment of the tag 24 to the sponge (not shown) at the tab 32 may be less likely to damage the electronics and antenna of the identifier 10 during the attachment process.

Figure 11:
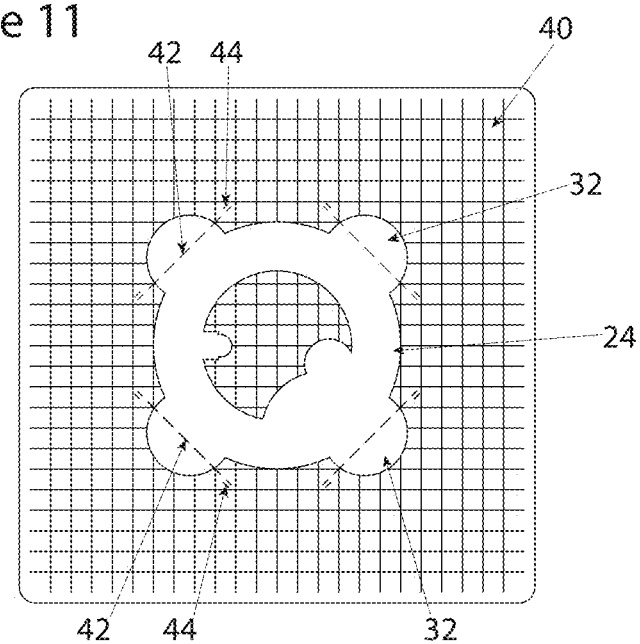
FIG. 11 is a top view of a surgical sponge according to a non-limiting illustrative embodiment having a tag according to any of the illustrated embodiments sewn to the sponge.

FIG. 11 illustrates a sponge provided with a tag according to an exemplary embodiment. In the illustrated embodiment of FIG. 11, the tag 24 can be sewn to the sponge 40, though, other methods of securely attaching the tag 24 to the sponge 40 is contemplated within the scope of the present disclosure. The tag 24 can be attached to the sponge 40 by sewing through both the sponge material 40 and the base layer and protective film layer of the tag 24. Sewing through the one or more tabs 32 (e.g., along marks 42) reduces the chance of cutting a foil trace of the antenna, a printed conductive ink trace or a wire of the antenna with the sewing needle. The tab 32 also allows the backstitch anchoring 44 of the sewing seam 42 to occur off the side edge of the tab 32, in the sponge material 40 only. The sewing seam 42 may cross the tab but may be backstitch anchored 44 adjacent each side of the tab 32 in the sponge material 40. The multiple sewing pierces created by a backstitch anchor seam 44, could substantially weaken the film laminate and allow tearing of the film to start at that location if the backstitching 44 were to land on the tab 32.

Figure 12:
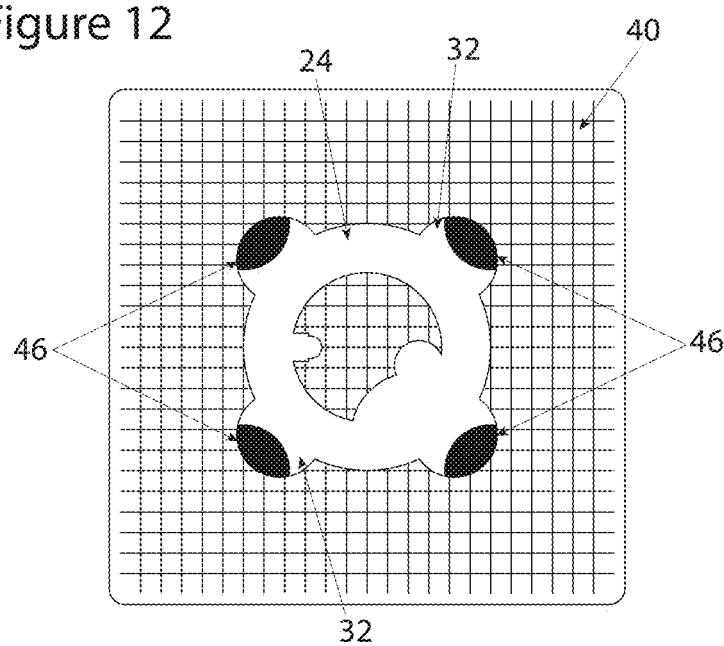
FIG. 12 is a top view of a surgical sponge according to another non-limiting illustrative embodiment having a tag according to any of the illustrated embodiments heat bonded to the sponge.

As shown in FIG. 12, in some embodiments, the one or more tabs 32 may be a safe area for heat bonding 46 the tag 24 to the sponge 40. Heat bonding may be accomplished by applying a hot object to one or more layers of the sponge fabric 40 while pushing the threads of the fabric down onto the one or more protective film layers of the tab 32. The heated object warms and partially melts the polymeric film, embedding the threads of the sponge 40 into the melted film 46. When the polymeric film cools, the fabric of the sponge 40 is securely adhered to the plastic film of the tag 24. The tabs 32 create an area for heating that is geographically separated from the from the antenna trace 12 and electrically responsive member 16 of the identifier, thus reducing the potential of damaging the identifier during the process of heat bonding the sponge 40 to the tag 24.

Figure 13:
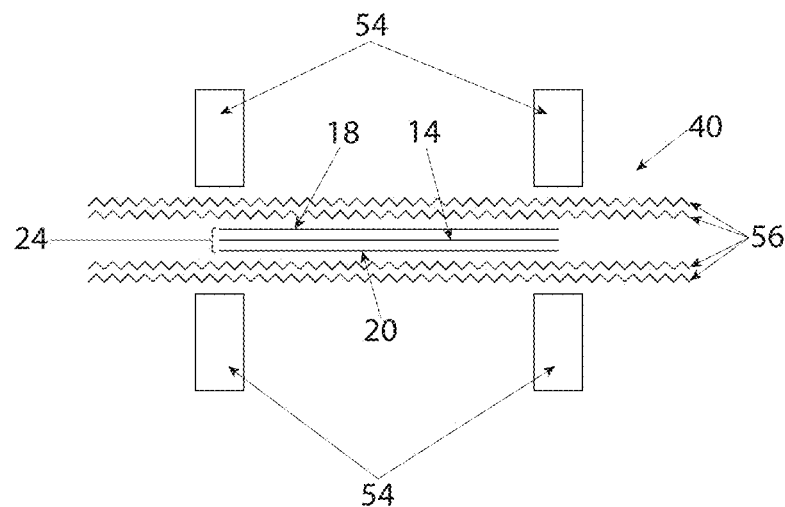
FIG. 13 is a schematic illustrating a method of manufacturing surgical sponges that include tags according to an exemplary embodiment.
Figure 14:
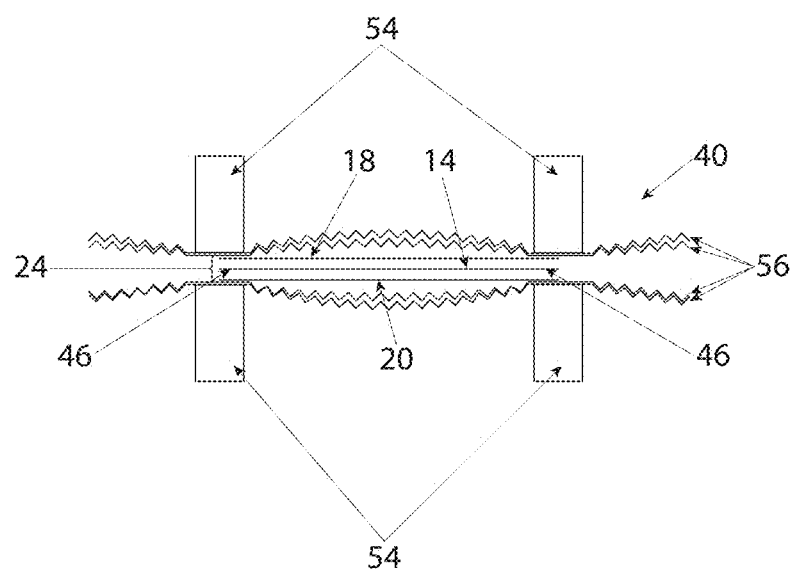
FIG. 14 is a schematic illustrating a method of manufacturing surgical sponges that include tags according to another exemplary embodiment.

Heat bonding 46 may be advantageous if an automated manufacturing process is used for manufacturing the sponges. Accordingly, the present disclosure provides a method of manufacturing surgical sponges that include tags 24 or markers (markers are tags without an inlay RFID identifier) that have an outer protective layer 18, 20 of polymeric film. FIGS. 13 and 14 illustrate some such exemplary embodiments. In an example, a method of manufacturing surgical sponges 40 includes folding a sheet of gauze fabric 56 one or more times and interposing the tag 24 or marker between the folded layers of gauze fabric 56. As shown in FIG. 14, one or more heated metal members 54 maybe pushed against the one or more layers of gauze fabric 56, pushing the gauze fabric 56 firmly against the polymeric film 18, 20. The one or more heated metal members 54 are shaped, positioned and indexed to apply heat to areas of the tag 24 or marker that will not be damaged by the heat 46.

The heated metal member 54 is heated to a temperature that is greater than the melting point of the selected polymeric film 18, 20. The heat from the heated metal member 54 melts the polymeric film 18, 20 and the pressure against the gauze fabric 56 from the heated metal member 54 pushes one or more layers of the fabric 56 into the melted polymeric film 18, 20. The heated metal member 54 is then retracted from the fabric 56, and as the melted polymeric film layer 18, 20 cools, it bonds to the embedded gauze fabric 56. Applying the heat through the gauze fabric 56 may reduce the chances of the melted polymeric film 18, 20 from adhering to the heated metal member 54. If speed is desirable, the heated metal member 54 may be heated to a temperature significantly greater than the melting temperature of the polymeric film 18, 20. The folding of the gauze fabric 56, the indexing of the tag 24 or marker within the layers of gauze fabric 56 and the application of heat from the heated metal member 54 may be automated for economical manufacturing.

FIG. 14 illustrates a method of manufacturing sponges according to another exemplary embodiment. In the embodiment of FIG. 14, heat may be simultaneously applied to both sides of the sponge thus heat bonding the gauze fabric 56 to both sides of the tag 24. Applying the heat simultaneously to both sides of the tag 24, reduces the time required to melt the polymeric film 18, 20 and create a bond with the gauze fabric 56. Alternatively, it is anticipated that the heat may be applied to only one side of the tag 24.

Referring back to FIGS. 11 and 12, in certain exemplary embodiments, an attached, flexible RFID or RF inlay tag 24 may also be attached to the sponge 40 according to the above-disclosed method of manufacturing surgical sponges. The attachment location between the sponge 40 and the tag 24 may be at the one or more tabs 32. Because the tabs 32 are physically separated from the functional parts of the identifier 10, less precision is sufficient when applying pressure and heat or piercing with sewing needles to avoid damaging the identifier 10, and thereby permitting automation of the manufacturing process.

As mentioned above, the one or more tabs become a safe and flexible area for adhesively bonding the tag to the sponge. Fast curing adhesives such as epoxy are frequently stiff. Applying a stiff adhesive to the tag 24 may result in a stiff tag 24. Applying a stiff adhesive to a tab 32 may maintain the general flexibility of the tag 24.

As shown by the non-limiting illustrative embodiment of FIG. 9, the metal foil inlay identifier 12 or the metal wire of a loop antenna 12 creates a densely radio-opaque area that is easy to visualize by x-ray. Metal foil or wire is much more radio-opaque than barium sulfate. In some embodiments, extra conductive ink may be applied, especially conductive inks that contain metals, to increase the radio-opacity of the tag.

Excess metal foil 48 may be purposefully left on the base layer 14 during the etching process, substantially increasing the square area of the metal foil x-ray opacity at no extra cost. The extra metal foil 48 may or may not be electrically connected to the antenna 12. The extra foil adds additional radio-opacity to the tag for better x-ray visualization. In some such aspects, the extra metal foil 48 may be located substantially within the outer perimeter 34 of the tag 24. In addition, the extra metal foil 48 may be located substantially outside the outer perimeter 34 of the tag 24.

With continued reference to FIG. 9, the extra metal foil 48 may be located in the one or more tabs 32. The tabs 32 can fold and bend relative to the main body of the tag 24. Including a layer of metal foil 48 in the tabs 32 therefore increases the probability of some of the foil 48 being oriented substantially perpendicular to the x-ray beam when the sponge (not shown) is crumpled into a three dimensional wad-shape and left in the body.

The protective layer of polymeric film 18, 20 may optionally be colored. For instance, the protective layer of polymeric film 18, 20 may not be clear. Additionally, the protective layer 18, 20 may be coated with pigment to make the tag 24 more visible to the surgeon. Bright colors may contrast with blood and tissue and therefore improve visibility. Suitable colors include but are not limited to: green, yellow, purple, blue and white. In an example, the protective layer 18, 20 can be coated with simple bright pigments or "neon" or "fluorescent" pigments, for instance, those made by the DayGlo Color Corp. (Cleveland, Ohio).

Continuing with the advantageous exemplary aspects described above, the protective layers 18, 20, when coated with pigments may optionally "fluoresce" when illuminated by UV light or colored lights, causing the fluorescent pigments in the tag 24 to become more visible. For instance, particles or spheres of material such as glass or plastic that reflect light may be embedded in the polymeric film. Alternatively, a layer of reflective film may be used for one or more of the protective film layers 18, 20. In further aspects of the disclosure, one or more layers of reflective film may be laminated to the one or more protective film layers 18, 20.

In certain exemplary embodiments, the one or more protective film layers 18, 20 maybe made of a substantially hydrophobic polymeric material to prevent blood from coating the brightly colored film and obscuring the tag 24 or marker from the surgeons view. Alternatively, a hydrophobic material may be coated on to the protective layers 18, 20. For instance, polymeric films that are hydrophobic relative to the absorbent, hydrophilic properties of a fabric sponge are contemplated for use. Additionally, the surface of the protective film layers 18, 20 may be coated with a hydrophobic material that further enhances the hydrophobic nature of the film.

Enhanced surgical sponge visualization and/or enhanced surgical sponge x-ray opacity may be desirable without RFID. Accordingly, in certain cases, inexpensive and easily identifiable polymeric film "markers" may be made similarly to the RFID tags 24 previously discussed except that the inlay identifier 10 is omitted. For instance, the markers may be made of one or more layers of colored, hydrophobic polymeric film 18, 20 as previously discussed for RFID tags. The markers may include a metal foil layer for x-ray opacity.

The marker may be any size or shape that can fit within the area of a sponge. In some cases, the marker may include tabs 32 as previously disclosed on tag 24. The polymeric film marker may then be positioned between the layers of the surgical sponge. As shown by the non-limiting example of FIG. 10, and as described previously, tabs 32 may extend radially outward from the outer perimeter of the marker and the radial extension may be positioned to extend beyond the perimeter of the sponge (not shown). In this location, the colored marker is more visible to the surgeon when the sponge is in the patient and the sponge is saturated in blood.

Without RFID tags, these sponges with markers will have to be hand-counted by the nurse. Colored markers extending beyond the edge of the surgical sponges are much easier to identify individually and count than is a stack of homogeneous white sponges. Exposed tabs 32 may reduce the need to unfold each blood-laden sponge to assure that two sponges are not stuck together during manual counting. This makes manual counting much easier and faster.

The colored marker may optionally be attached to the fabric of the sponge by heat bonding or sewing as previously described for a tag 24. As illustrated by the exemplary embodiment of FIGS. 13 and 14, heat bonding or sewing the marker to the sponge may allow the surgical sponge manufacturing process to be automated, and thereby more economic.

While the description generally focuses on attachment of brightly colored flexible markers or RFID tags 24 to surgical sponges, a skilled artisan would appreciate that such markers or RFID tags 24 described in the present disclosure may also be attached to other surgical articles for enhanced visual identification or RFID identification. The bright colors of a tag 24 or marker make the surgical item easier to see both inside and outside the patients' body. Other surgical items may include but are not limited to: surgical instruments, pledgets, cannulas, tubing, drains, stints, clamps, foam, retractors and sutures.

Traditionally a number of surgical sponges (e.g., a set of five or ten sponges) may be packaged together (e.g., stacked on top of each other). If smaller sponges that contain RFID tags are packaged side-by-side in a bundle, the RFID antennae may proximate each other and cause interference or "coupling" during the sponge entry process.

Figure 15:
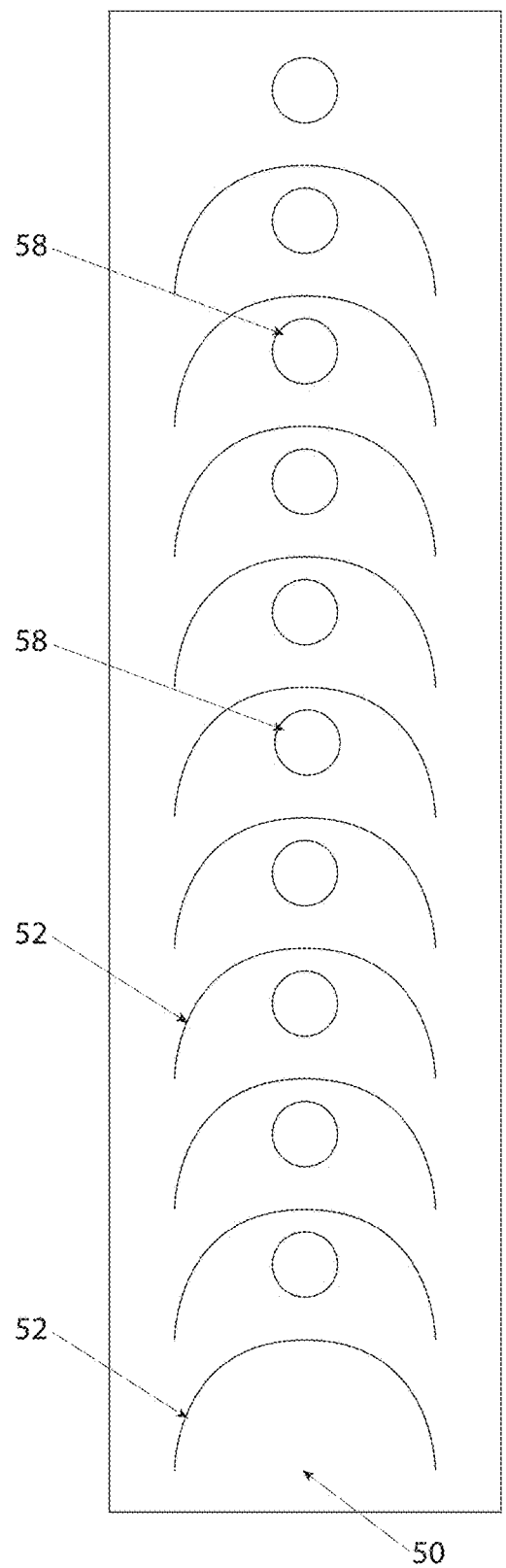
FIG. 15 is a schematic illustrating a packaged bundle of sponges according to a non-limiting exemplary embodiment.
Figure 16:
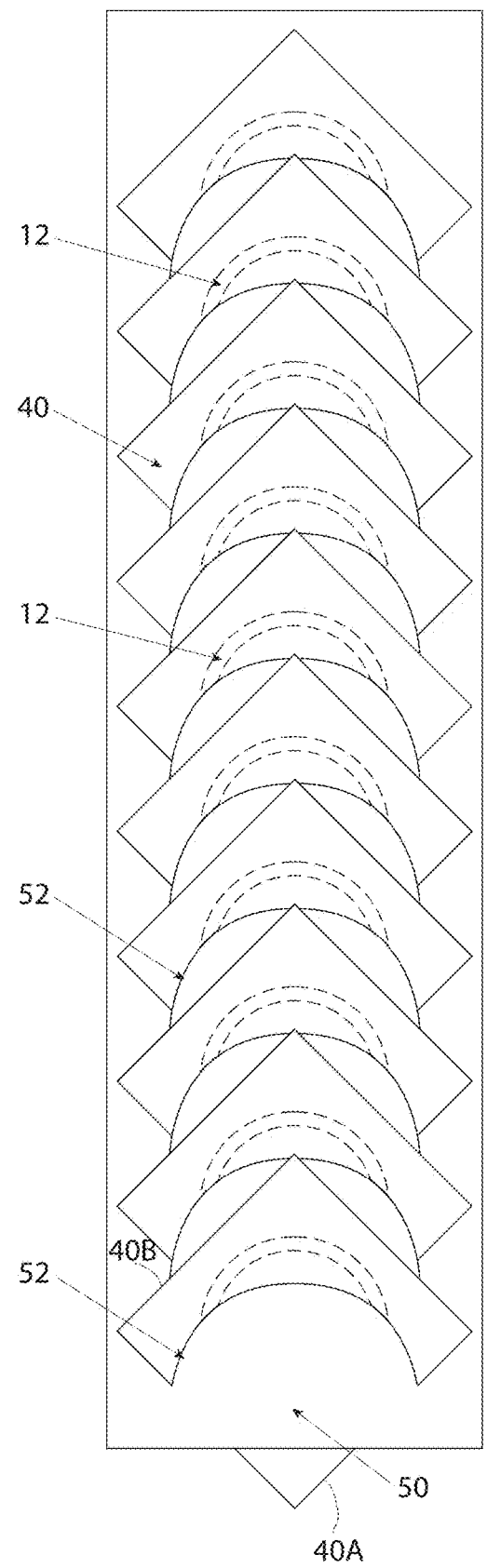
FIG. 16 is a schematic illustrating a packaged bundle of sponges according to a non-limiting exemplary embodiment.

FIGS. 15 and 16 illustrate a packaged bundle of sponges according to a non-limiting exemplary embodiment. While FIGS. 15 and 16 illustrate a package of sponges, other surgical articles including but not limited to: surgical instruments, pledgets, cannulas, tubing, drains, stints, clamps, foam, retractors and sutures may also be used instead of sponges. As seen by the embodiments of FIGS. 15 and 16, the sponges 40 may be removably attached to a sponge dispensing card 50. The sponge dispensing card 50 can spread the sponges 40 out so that their antennae 12 only partially overlap, decreasing the chances of "coupling."

The sponge dispensing card 50 may be made of cardboard or plastic in some cases. The sponge dispensing card 50 may be of any shape including but not limited to round, square and rectangular.

In an example, the sponges 40 may be attached to the sponge dispensing card 50 by one or more slits 52 in the card 50 through which a portion of the sponge 40 can pass. The slits 52 may spread the sponges 40 out over the face of the card 50 and retain the sponge 40 and yet allow ease of removal of the sponge 40 from the sponge dispensing card 50. The slits 52 through the card 50 may be generally straight, generally semi-circular, angled or any other shape and length. A semi-circular slit 52 may be advantageous during the process (e.g., an automated process) of loading the sponge 40 into the slit 52. A semi-circular slit 52 allows a greater opening of the space for insertion of the sponge 40. The slits 52 can additionally reduce the possibility of adhesive from sticking to the material of the sponge 40 upon removal from the card 50. The slits 52 can be sized to allow between about ⅓ and about ⅔ of the area of each sponge to fit through the corresponding slit 52. When inserted as such at least opposite edges 40A and 40B of each sponge can be positioned on the opposite side of the card.

As illustrated in FIGS. 15 and 16, according to an embodiment, sponges 40 can be attached the sponge dispensing card 50 by a releasable adhesive. In some embodiments, the attachment of sponges 40 to the sponge dispensing card 50 may be made by folding the card 50 to create a pocket that can accommodate a portion of each sponge. Other attachment methods are anticipated. When assembled according to some exemplary embodiments, the sponges 40 may be spread out over the surface of the sponge dispensing card 50 so that their antennae may overlap or crossover but do not stack.

Spreading the sponges 40 out over the surface of the sponge dispensing card 50 also decreases the chances of erroneously packaging the wrong number of sponges 40 in the pack at the factory. If each location on the sponge dispensing card 50 is occupied by a single sponge 40, the correct number of sponges 40 can be reliably identified with a cursory visual or machine inspection during the manufacturing process. Added visibility for a cursory inspection can be achieved by adding a colored spot 58 to the card 50 in a location that will be covered and obscured by properly inserted sponges 40. Any missing sponge 40 will expose the easily identifiable bright colored spot 58. To prevent two sponges 40 from being inadvertently inserted into a single slit 52, the length of the slit 52 may be limited to a shorter length that does not accommodate two sponges. In the alternative, if the sponges are in a stack, they may be hand separated and counted one at a time to determine if the right number is in the package.

In some embodiments, spreading the sponges 40 out over the surface of the sponge dispensing card 50 may allow the nurse or surgical technician to quickly and accurately visually count the sponges 40 during the entry process. If each location on the sponge dispensing card 50 is occupied by a single sponge 40, the correct number of sponges 40 can be reliably identified with a cursory visual inspection rather than the manual counting of the sponges 40. This may be advantageous in the case of sponges 40 that contain markers that do not have RFID or RF capability and therefore may have to be counted manually.

In some embodiments, the sponge dispensing card 50 may include a pressure sensitive adhesive area designed to stick the card to the surgical instrument table. This pressure sensitive adhesive may secure the card 50 to the table allowing easier dispensing of the sponges 40 from the card 50.

Various examples have been described. These and other examples are within the scope of the following claims.

The invention claimed is:

1. A surgical sponge, comprising:
   a sponge body; and
   a radiofrequency (RF) tag positioned interior to the sponge body, the tag comprising:
     a base layer, the base layer comprising a first polymeric film material,
     a first protective layer having at least one tab projecting from an outer perimeter of the tag, the first protective layer comprising a second polymer material, and
     a radiofrequency (RF) identifier laminated between the base layer and the first protective layer, comprising a loop antenna and an electrically responsive member,
   wherein the base layer and the first protective layer are not present at a portion of an area of the tag defined by an inner perimeter of the loop antenna, thereby creating a hole through the tag, and
   wherein one or more attachment tabs of the base layer and the first protective layer project inward from the inner perimeter of the loop antenna, each of the one or more attachment tabs defining a perimeter edge portion of the hole, and an entire perimeter of the hole being spaced from an outer perimeter of the tag, at least a portion of the electrically responsive member being located in one of the one or more attachment tabs.

2. The surgical sponge of claim 1, wherein the antenna is at least one of an etched metal foil loop antenna and a wound wire loop antenna.

3. The surgical sponge of claim 1, wherein the electrically responsive member includes at least one of programmable integrated circuit (IC) chip, a capacitor, and a resistor.

4. The surgical sponge of claim 1, wherein the tag includes a second protective layer positioned opposite to the first protective layer, the second protective layer comprising a polymeric film material, the second protective layer and the first protective layer substantially enclosing the base layer and the identifier.

5. The surgical sponge of claim 4, wherein the polymeric film material of the second protective layer is a flexible tear-resistant film.

6. The surgical sponge of claim 1, wherein the tag is attached to the sponge body at a location corresponding to the at least one tab of the first protective layer.

7. The surgical sponge of claim 1, wherein one or more tabs of the first protective layer project radially outward beyond an edge of the sponge body when the tag is attached to the sponge body.

8. The surgical sponge of claim 7, wherein the one or more tabs of the first protective layer that project radially outward beyond an edge of the sponge body when the tag is attached to the sponge body are formed into a substantially D shaped handle.

9. The surgical sponge of claim 7, wherein the tag includes a second protective layer positioned opposite to the first protective layer, the second protective layer comprising a polymeric film material, the second protective layer and the first protective layer substantially enclosing the base layer and the identifier, wherein one or more of the base layer and the first and second protective layers is made of colored polymeric film so as to contrast with blood and tissue.

10. The surgical sponge of claim 7, wherein the tag includes a second protective layer positioned opposite to the first protective layer, the second protective layer comprising a polymeric film material, the second protective layer and the first protective layer substantially enclosing the base layer and the identifier, wherein one or more of the first and second protective layers is configured to fluoresce when illuminated by a light source at a predetermined wavelength.

11. The surgical sponge of claim 7, wherein the tag includes a second protective layer positioned opposite to the first protective layer, the second protective layer comprising a polymeric film material, the second protective layer and the first protective layer substantially enclosing the base layer and the identifier, wherein the first and second protective layers are hydrophobic relative to the surgical sponge, the first and second protective layers being configured for repelling blood.

12. A surgical sponge, comprising:
   a sponge body; and
   a radiofrequency (RF) tag attached within an interior portion of the sponge body, the tag comprising:
     a base layer,
     a metal foil loop antenna etched on to the base layer,
     an electrically responsive member,
     additional metal foil provided on the base layer, wherein the additional metal foil comprises excess metal foil left on the base layer when the metal foil loop antenna is etched on to the base layer, the additional metal foil configured to enhance x-ray opacity of the surgical sponge, and
     a first polymeric film protective layer with the metal foil loop antenna and the electrically responsive member being laminated between the first polymeric film protective layer and the base layer, a second protective layer positioned opposite to the first polymeric film protective layer, the second protective layer comprising a polymeric film material, the second protective layer and the first polymeric film protective layer substantially enclosing the base layer, the metal foil loop antenna, and the electrically responsive member, wherein the base layer, the first polymeric film protective layer and the second protective layer are not present at a portion of an area of the tag defined by an inner perimeter of the loop antenna, thereby creating a hole through the tag, and wherein one or more attachment tabs of the base layer, the first polymeric film protective layer and the second protective layer project inward from the inner perimeter of the loop antenna, each of the one or more attachment tabs defining a perimeter edge portion of the hole, and an entire perimeter of the hole being spaced from an outer perimeter of the tag, at least a portion of the electrically responsive member being located in one of the one or more attachment tabs.

13. The surgical sponge of claim 12, wherein the electrically responsive member includes at least one of programmable integrated circuit (IC) chip, a capacitor, and a resistor.

14. The surgical sponge of claim 12, wherein the one or more attachment tabs of the base layer and the first polymeric film protective layer that project inward from the inner perimeter of the loop antenna include a layer of metal foil configured for enhancing x-ray opacity of the surgical sponge.

15. The surgical sponge of claim 12, wherein one or more tabs of the base layer and the first polymeric film protective layer project outward from an outer perimeter of the tag, the one or more tabs that project outward from the outer perimeter of the tag including a layer of metal foil configured for enhancing x-ray opacity of the surgical sponge.

16. The surgical sponge of claim 15, wherein the one or more tabs of the base layer and the first polymeric film protective layer that project outward from the outer perimeter of the tag are formed into a substantially D shaped handle that projects radially outward beyond an edge of the sponge body when the tag is attached to the sponge body.

17. The surgical sponge of claim 12, wherein the tag is attached to the sponge body at a location corresponding to the one or more attachment tabs of each of the first polymeric film protective layer and the base layer by at least one of sewing and heat bonding.

18. The surgical sponge of claim 17, wherein fibers of the surgical sponge are pressed into polymeric film material of the tag that has been heated and partially melted, creating a heat bond between the fibers and the polymeric film material.

19. The surgical sponge of claim 12, wherein one or more of the base layer, the first polymeric film protective layer, and the second protective layer is made of colored polymeric film so as to contrast with blood and tissue.

20. The surgical sponge of claim 12, wherein the surgical sponge is one of a plurality of countable and detectable surgical sponges configured to be mounted on a dispensing card, the dispensing card including a plurality of substantially transverse slits arranged along a longitudinal axis with each slit being spaced apart from an adjacent slit and each surgical sponge being insertable into a corresponding slit in order to spread the surgical sponges out across a surface of the dispensing card, so that the metal foil loop antennas of the surgical sponges are minimally overlapping in order to reduce electrical coupling between the antennas of adjacent surgical sponges.

21. A surgical sponge, comprising:
a fabric sponge body; and
a radiofrequency (RF) tag attached within an interior portion of the sponge body, the tag comprising:
a base layer,
a metal foil loop antenna etched on to the base layer,
an electrically responsive member,
additional metal foil provided on the base layer, wherein the additional metal foil comprises excess metal foil left on the base layer when the metal foil loop antenna is etched on to the base layer, the additional metal foil configured to enhance x-ray opacity of the surgical sponge, and
a first polymeric film protective layer with the metal foil loop antenna and the electrically responsive member being laminated between the first polymeric film protective layer and the base layer,
wherein the base layer and the first polymeric film protective layer are not present at a portion of an area of the tag defined by an inner perimeter of the loop antenna, thereby creating a hole through the tag, the hole being configured to improve stretchability or planar deformation of the tag as compared to an identical tag without the hole,
wherein one or more attachment tabs of the base layer and the first polymeric film protective layer project inward from the inner perimeter of the loop antenna, each of the one or more attachment tabs defining a perimeter edge portion of the hole, and an entire perimeter of the hole being spaced from an outer perimeter of the tag, at least a portion of the electrically responsive member being located in one of the one or more attachment tabs.

22. The surgical sponge of claim 1, wherein the inner perimeter of the loop antenna surrounds an entirety of the hole.

23. The surgical sponge of claim 12, wherein the inner perimeter of the loop antenna surrounds an entirety of the hole.

* * * * *